United States Patent [19]
Yamamoto

[11] Patent Number: 5,968,015
[45] Date of Patent: Oct. 19, 1999

[54] INJECTOR HEAD FOR MEDICAL USE

[75] Inventor: Tetsuya Yamamoto, Osaka, Japan

[73] Assignee: Sugan Co., Ltd., Osaka, Japan

[21] Appl. No.: 09/034,995

[22] Filed: Mar. 5, 1998

[30] Foreign Application Priority Data

Mar. 5, 1997 [JP] Japan ..................... 9-050410

[51] Int. Cl.⁶ .................. A61M 5/142; A61M 5/20
[52] U.S. Cl. ..................... 604/155; 128/DIG. 1; 604/154
[58] Field of Search ................. 604/152, 154, 604/155; 128/DIG. 1, DIG. 12

[56] References Cited

U.S. PATENT DOCUMENTS

| | | | |
|---|---|---|---|
| 3,720,211 | 3/1973 | Kyrias | 604/155 |
| 4,108,177 | 8/1978 | Pistor | 604/155 |
| 4,191,187 | 3/1980 | Wright | 128/DIG. 1 |
| 4,407,659 | 10/1983 | Adam | 604/155 |
| 5,106,375 | 4/1992 | Conero | 604/155 |
| 5,322,511 | 6/1994 | Armbruster et al. | 604/155 |
| 5,505,697 | 4/1996 | McKinnon, Jr. et al. | 604/155 |
| 5,505,709 | 4/1996 | Funderburk et al. | 604/155 |
| 5,647,853 | 7/1997 | Feldman et al. | 604/155 |
| 5,722,956 | 3/1998 | Sims et al. | 604/154 |

*Primary Examiner*—Paul J. Hirsch
*Attorney, Agent, or Firm*—McDermott, Will & Emery

[57] ABSTRACT

An injector head for medical use is provided with a position plate serving as both the position plate and a nut, placed at a rear end portion of a plunger, as well as a screw axis engaging with the position plate. A mechanical stopper which can slide only in a direction of an axis of the plunger is provided to the plunger. A female thread is formed on the surface of the mechanical stopper. A main body portion is provided which accommodates the mechanical stopper, the plunger, and the position plate and has a male thread formed on its inner surface and screwed together with the female thread. By utilizing this structure, an injector head for medical use can be provided which is scaled down and simplified while keeping its mechanical safety mechanism.

8 Claims, 15 Drawing Sheets

_5,968,015_

INJECTOR HEAD FOR MEDICAL USE

BACKGROUND OF THE INVENTION

1. Field of the Invention

The present invention relates to an injector head for medical use, and more particularly relates to an improvement of the structure of the injector head for medical use.

2. Description of the Background Art

Various apparatuses for testing the function of the human body have been developed recently. One example is a circulatory organ X-ray diagnostic apparatus for diagnosing the function of the circulatory organ of the human body. With reference to FIG. 15, a general description of the circulatory organ x-ray diagnostic apparatus will be given.

A circulatory organ X-ray diagnostic apparatus 1000 is provided with a rail 103 attached to a ceiling 101. An X-ray apparatus 102 which is movable freely in X and Y directions is attached to rail 103. A cartheter table 104 for laying a patient 106 at a prescribed position is arranged at a prescribed position.

A side of cartheter table 104 has a guide rail 108. Guide rail 108 has an equipment attached for performing the procedure necessary for the X-ray diagnosis for patient 106. In FIG. 15, for example, a support unit 200 is mounted on guide rail 108, and an injector head for medical use 100 for injecting the contrast medium into patient 106 is attached to support unit 200 via a stanchion 114. By moving support unit 200 along guide rail 108, medical injector head 100 can be positioned at patient 106, and interference with any other apparatus can be avoided.

With reference to FIGS. 16 and 17, a structure of medical injector head 100 is generally described. Note that FIG. 16 is a perspective view illustrating an internal structure of medical injector head 100 and FIG. 17 shows an arrangement of internal units viewing from the rear side of medical injector head 100.

A syringe 120 having a piston 121 provided therein is attached to medical injector head 100. A plunger 122 provided to injector head 100 is coupled to piston 121. The contrast medium contained in syringe 120 can be injected to a patient by moving plunger 122 forward. On the other hand, backward movement of plunger 122 causes the contrast medium to be sucked in syringe 120.

A ball screw (not shown) is attached to a rear end of plunger 122. By rotating the ball screw using a plunger motor 130, forward and backward movements of plunger 122 can be controlled.

Plunger 122 is also provided with a position plate 123. Position plate 123 moves with plunger 122 following the movement of plunger 122. When position plate 123 meets a mechanical stopper 129 described below, the forward movement of plunger 122 is mechanically impeded. Accordingly, even if an electrical control device for medical injector head 100 fails, the safety of mechanical injector head 100 is assured by mechanically restraining plunger 122 from moving.

Four corners of position plate 123 are guided by guide rods 124 provided in a body frame 110.

Mechanical stopper 129 also serves as a nut of the ball screw. Mechanical stopper 129 can be positioned at a prescribed position by rotating a screw axis 128 of the ball screw. As shown in FIG. 17, mechanical stopper 129 is also guided by diagonally placed guide rods 124.

Screw axes 128a and 128b are placed at diagonal positions in mechanical stopper 129. Pulleys 127a and 127b are provided at the ends of screw axes 128a and 128b. A belt 126 is wound around pulleys 127a and 127b. A turning force of a mechanical stop motor 125 is transmitted to screw axes 128a and 128b via pulleys 127c and 127d. Positioning of mechanical stopper 129 can be controlled by utilizing a position meter (not shown) provided to mechanical stop motor 125.

A safety mechanism adopted by the injector head can be summarized as follows. Even if an electrical device for controlling plunger 122 fails and a signal which causes plunger 122 to move forward without stopping is transferred, position plate 123 comes into contact with mechanical stopper 129 placed at a prescribed position thereby mechanically stopping plunger 122.

The structure of the conventional injector head for medical use described above has a problem below.

Referring again to FIGS. 16 and 17, a hole 129h for passing plunger 122 therethrough is provided at the central portion of mechanical stopper 129 provided to medical injector head 100. In order to drive mechanical stopper 129 in a stable state such that it does not move out of its proper position, nut screws are placed diagonally at two positions.

Specifically, as shown in FIG. 18, suppose that a force applied from position plate 123 to mechanical stopper 129 is $f_1$, a reaction force $f_2$ is generated at the positions of the two nut screws supporting mechanical stopper 129. As a result, mechanical stopper 129 is brought into a stable state by force $f_1$ and reaction force $f_2$ at two positions. Mechanical stopper 129 is thus driven to function in the stable state without moving out of its proper position in the direction shown by A in the figure.

Since nut screws are placed at two positions of mechanical stopper 129, medical injector head 100 becomes large. Further, synchronized operation of two nut screws requires pulleys 127a, 127b, 127c, 127d and belt 126, resulting in a complex structure of the device.

SUMMARY OF THE INVENTION

An object of the present invention is to scale down and simplify an injector head for medical use while keeping the mechanical safety mechanism thereof.

An injector head for medical use according to the invention is provided with a syringe attached thereto. The syringe includes: a cylindrical body portion having an inject portion and an opening portion respectively at a front end side and a rear end side; and a piston provided movably between the front and back rear end sides of the body portion, the piston defining an internal space within the body portion for sucking in contrast medium to be injected into a body of a patient. The injector head for medical use includes: a plunger which has its front end coupled to the piston, and is capable of reciprocating in the direction of the movement of the piston and restrained from rotating on its own axis; a first drive unit provided at the rear end of the plunger for allowing the plunger to reciprocate; a mechanical stopper through which the plunger passes, and which is provided such that it is capable of moving in a direction of the axis of the plunger and restrained from rotating on the axis of the plunger; a move and fix unit for moving the mechanical stopper in the direction of the axis of the plunger and for fixing the mechanical stopper at an arbitrary position by engaging with the mechanical stopper while rotating on the axis of the plunger; a second drive unit for rotating the move and fix unit; a position plate provided at the rear end side of the plunger to the rear of the mechanical stopper for preventing the movement of the plunger by contacting with the mechanical stopper when the plunger moves to the front end side; and a frame for supporting the plunger, the first drive unit, the mechanical stopper, the move and fix unit, and the position plate.

Preferably, the first drive unit includes: a ball screw having a screw axis placed such that it is accommodated by the plunger and a nut provided at the rear end of the plunger and screwing on the screw axis, and a drive mechanism for applying a turning force to the screw axis. The nut also serves as the position plate.

More preferably, the plunger includes a first concave and convex formed on its surface along the direction of its axis, and is supported by the frame member in the vicinity of its front end such that it is capable of sliding and restrained from rotating. The mechanical stopper includes a second concave and convex engaging with the first concave and convex on its inner surface as well as a first thread groove on its outer surface. The move and fix unit has a cylindrical shape and accommodates the ball screw and the position plate. The move and fix unit is provided with a main body having a second thread groove on its inner surface screwing on the first thread groove of the mechanical stopper.

The mechanical stopper has thus its inner surface provided with the second concave and convex engaging with the first concave and convex of the plunger, and its outer surface provided with the first thread groove. Further, the move and fix unit which has the main body portion accommodating the mechanical stopper is provided. The main body portion has its inner surface having the second thread groove screwing on the first thread groove. Since the first thread groove and the second thread groove are screwed together by rotating the plunger on its axis using the second drive unit, the mechanical stopper can be moved in the direction of the axis of the plunger along the first concave and convex of the plunger engaging the second concave and convex provided to the mechanical stopper.

On the other hand, even if the position plate is brought into contact with the mechanical stopper, the mechanical stopper would not be pushed to move in the direction of the axis of the plunger and can mechanically stop the position plate since the first thread groove of the mechanical stopper and the second thread groove of the move and fix unit are screwed together.

The mechanical stopper and the position plates are thus arranged on the same axis, so that the direction in which forces act on each other is in a single line. As a result, the structure of the medial injector head is simplified compared with the conventional one, and the injector head can thus be scaled down while keeping its mechanical safety mechanism.

Preferably, the plunger is supported by the frame member in the vicinity of the front end portion such that it is capable of sliding and restrained from rotating. The mechanical stopper includes the first thread groove on its inner surface and the second thread groove on its outer surface. The move and fix unit has a cylindrical shape accommodating some parts of the plunger and the nut of the ball screw. The move and fix unit includes: the main body portion having on its outer surface the third thread groove screwed together with the first thread groove as well as a slit exposing a part of the nut of the ball screw; and a gear arranged in parallel with the main body portion along the axis of the plunger, the gear having a fourth thread groove on its surface screwed together with the second thread groove of the mechanical stopper.

Accordingly, rotation of the gear causes the mechanical stopper to rotate. The mechanical stopper can thus be moved along the main body portion by screwing the first thread groove on the inner surface of the mechanical stopper and the third thread groove of the main body portion together.

The mechanical stopper and the position plate are thus arranged on the same axis so that the direction in which forces act on each other is in a single line. As a result, the structure of the medical injector head is simplified compared with the conventional medical injector head, and the injector head can be scaled down while keeping its mechanical safety mechanism.

Preferably, the move and fix unit further includes a detection unit for detecting that the position plate is brought into contact with the mechanical stopper.

The detection unit for detecting that the position plate meets the mechanical stopper stops a signal for electrically moving the plunger transferred to the first drive unit. As a result, the safety and reliability of the medical injector head can be improved.

Preferably, the frame includes a plunger rotation unit for selectively rotating the plunger by a prescribed angle. The plunger rotation unit provides easy attachment and detachment of the plunger to and from the piston. Accordingly, the working efficiency of an operator of the injector head for medical use can be enhanced.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS (First Embodiment)

Figure 1:
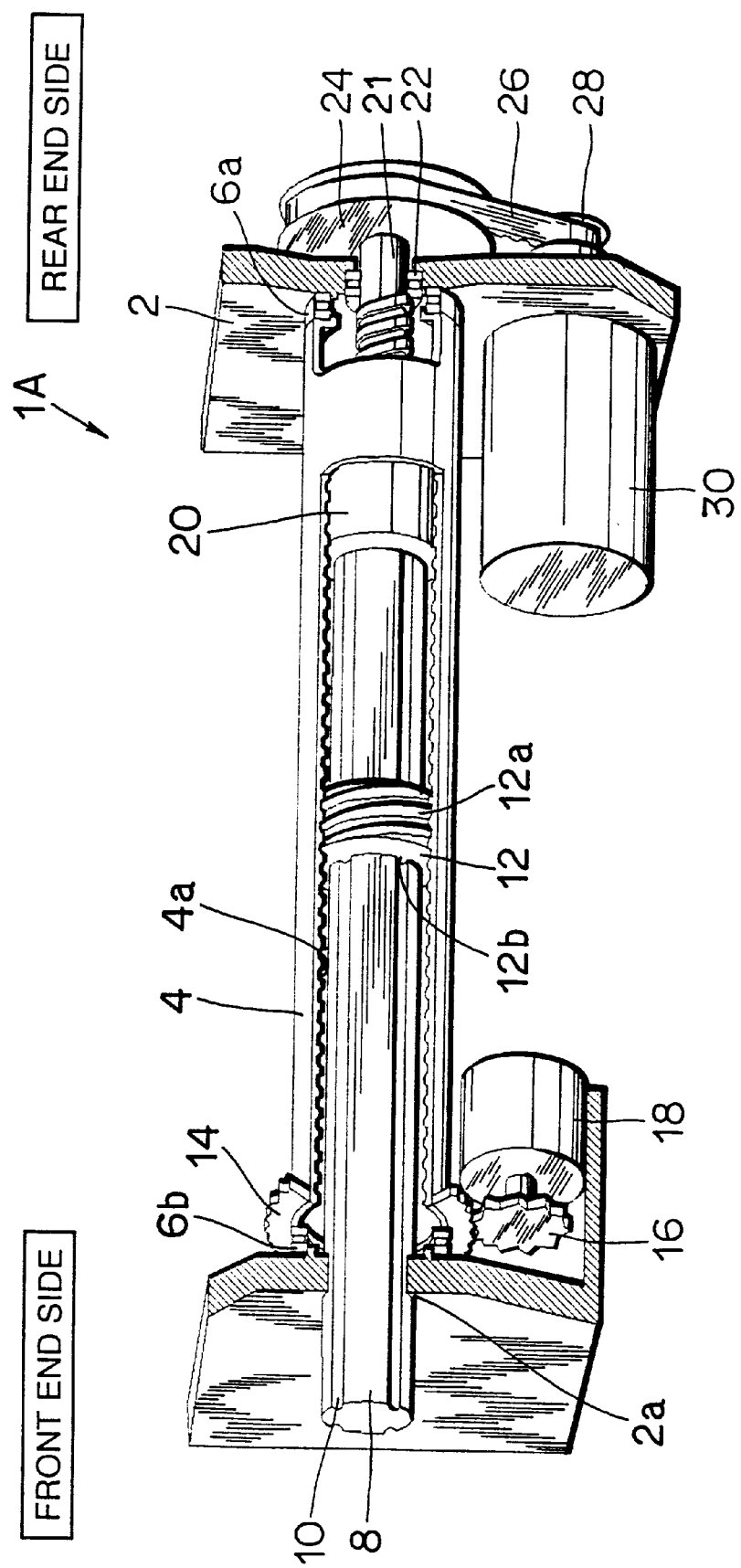
FIG. 1 is a partial cross section of an injector head for medical use according to the first embodiment of the invention.

Referring to FIG. 1, a structure of an injector head for medical use according to the first embodiment of the invention will be described.

An injector head for medical use 1A has a main body frame 2. A plunger 8 having its front end portion coupled to a piston (not shown) of a syringe is passed through a slide hole 2a provided to main body frame 2 such that plunger 8 can move in the direction of its axis.

An outer surface of plunger 8 has a plurality of concave grooves 10 along its axis. Slide hole 2a has a convex portion (not shown) engaging with concave groove 10 for restraining plunger 8 from rotating on its axis.

Plunger 8 has its rear end provided with a cylindrical position plate 20. Position plate 20 serves as both a position plate and a nut of a ball screw. The position plate and the nut of the ball screw can be provided as separate structures.

A front end portion of a screw axis 21 of the ball screw is placed in an internal space (not shown) of plunger 8 such that it does not interfere with plunger 8. On the other hand, a back end of ball screw 21 has a first pulley 24 attached thereto. The rear end side of screw axis 21 is supported by a bearing 22 provided to main body frame 2. A turning force of a plunger motor 30 attached to the main body frame 2 is transmitted by a second pulley 28 via a toothed belt 26 to the first pulley 24. Control of a reciprocating motion of plunger 8 is possible by controlling plunger motor 30.

Although the belt drive method is described as a method for transmitting the transmission force of plunger motor 30 to screw axis 21, a well known transmission mechanism can be employed. Screw axis 21 can be rotated, for example, using a servo motor.

A mechanical stopper 12 is fit onto plunger 8 ahead of the position plate 20. Mechanical stopper 12 has its inner surface provided with a convex portion 12b fit into a concave groove 10 of plunger 8. Although mechanical stopper 12 can be moved in the direction of the axis of plunger 8, it cannot be rotated on its axis. The convex portion and the concave groove may be provided respectively to plunger 8 and mechanical stopper 12, instead of providing to mechanical stopper 12 and plunger 8 respectively. A female thread 122a is formed on the outer surface of mechanical stopper 12. Further, Teflon coating is preferably applied to the surfaces of plunger 8 and mechanical stopper 12 in order to facilitate the movement of mechanical stopper 12 in the direction of the axis of plunger 8.

A cylindrical main body portion 4 accommodating plunger 8, mechanical stopper 12, position plate 20, and screw axis 21 is further provided. Both ends of main body portion 4 have thrust bearings 6a and 6b respectively attached thereto such that they can rotate on the axis of plunger 8 independently of main body frame 2.

Main body portion 4 has its inner surface having a male thread 4a screwing on female thread 12a on the outer surface of mechanical stopper 12. Accordingly, rotation of main body portion 4 allows mechanical stopper 12 to move along plunger 8. It is noted that the male and female threads may be formed respectively on the outer surface of mechanical stopper 12 and the inner surface of main body portion 4, instead of forming them respectively on the inner surface of main body portion 4 and the outer surface of mechanical stopper 12.

A first gear 14 is provided at the front end side of main body portion 4. The first gear engages with a second gear 16 which is driven to rotate by a mechanical stop motor 18. By controlling the rotation of mechanical stop motor 18, the rotation of main body portion 4 can be controlled. Further, the position of mechanical stopper 12 can be controlled. Although the rotation driving force from mechanical stop motor 18 for rotating main body portion 4 is transmitted using the gear train, another known method, for example, the well known belt driving may be employed.

Figure 2:
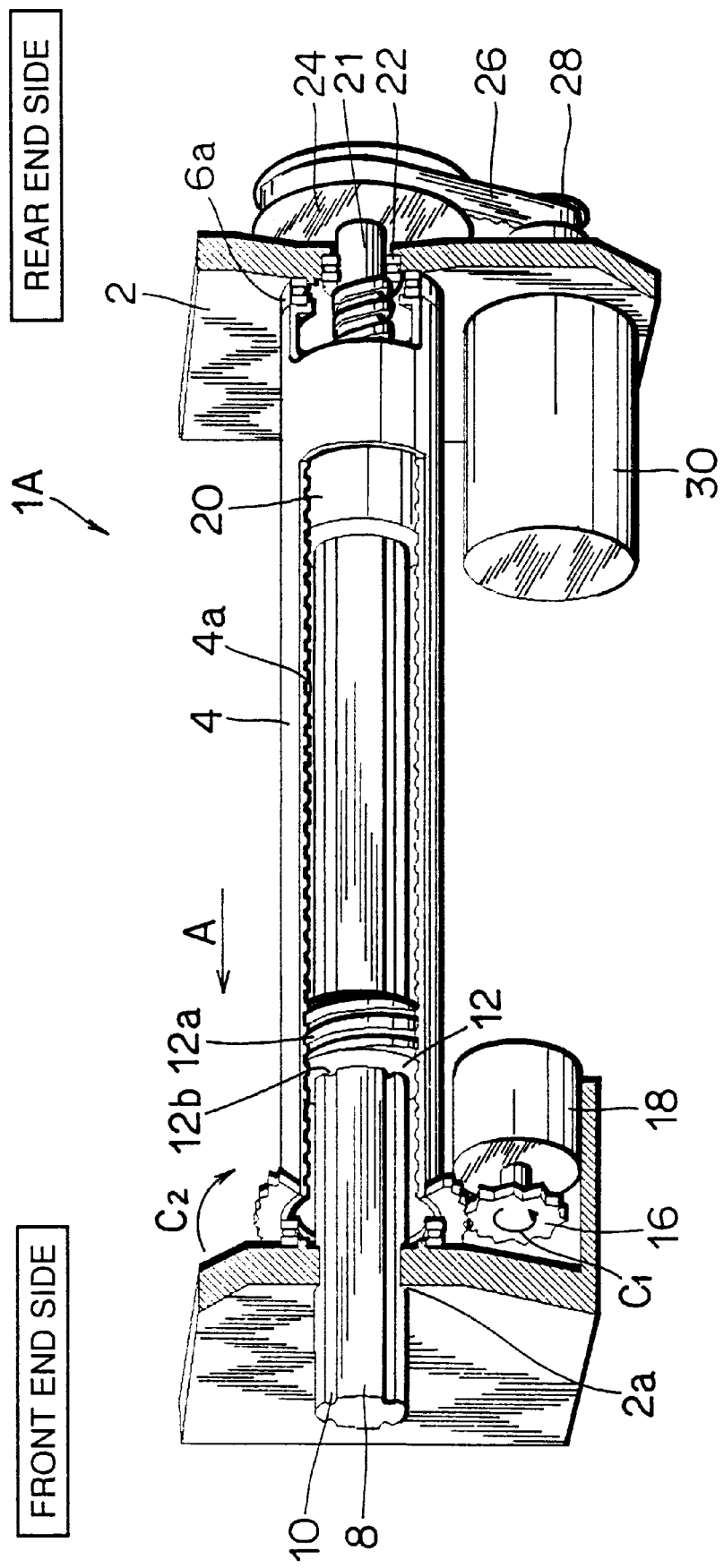
FIGS. 2 and 3 are respectively the first and second illustrations related to an operation of the medical injector head according to the first embodiment of the invention.

Referring to FIG. 2, a manner is described in which mechanical stopper 12 is moved along plunger 8 in medical injector head 1 having the structure described above. First, mechanical stop motor 18 is driven in the direction shown by $C_1$. The second gear 16 and the first gear 14 are accordingly rotated to cause rotation of main body portion 4 in the direction shown by $C_2$. Mechanical stopper 12 can thus be moved to the front end side (in the direction of A) of plunger 8.

Figure 3:
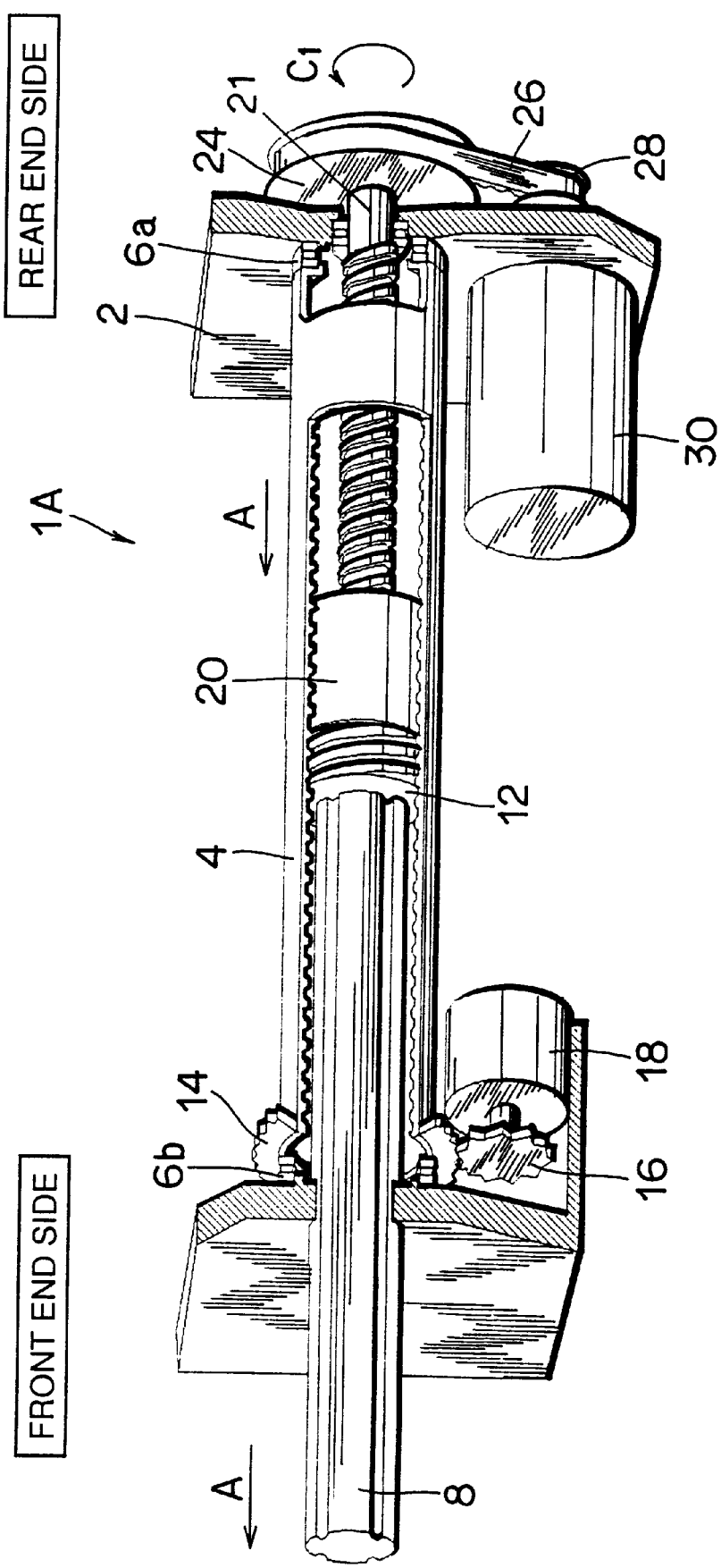

With reference to FIG. 3, a situation is described in which mechanical stopper 12 and position plate 20 meet when plunger 8 is moved to the front end side. Screw axis 21 is rotated in the direction shown by $C_1$ by driving plunger motor 30 to rotate. Accordingly, position plate 20 and plunger 8 move in the direction shown by the arrow A while the position of mechanical stopper 12 is fixed. When position plate 20 moves to the front end side, position plate 20 meets mechanical stopper 12 by the rotation of screw axis 21.

Figure 4:
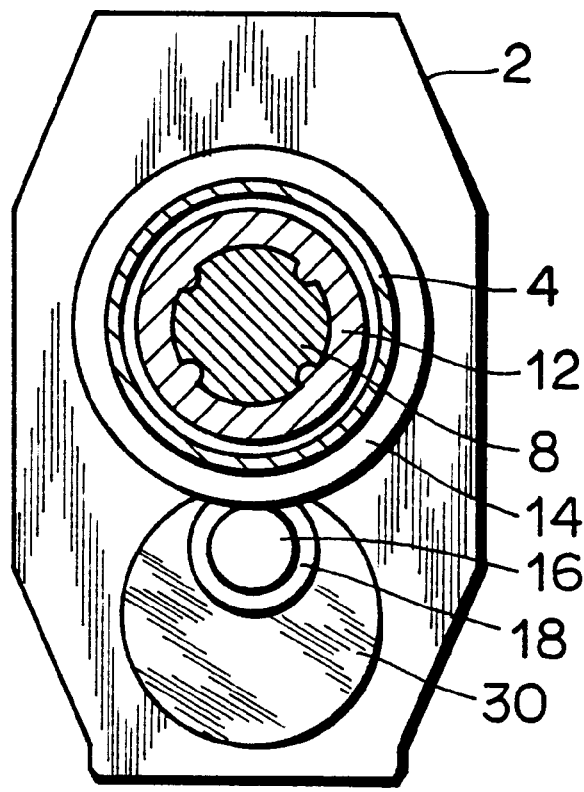
FIGS. 4 and 5 are respectively the first and second illustrations related to an effect of the medical injector head according to the first embodiment of the invention.
Figure 17:
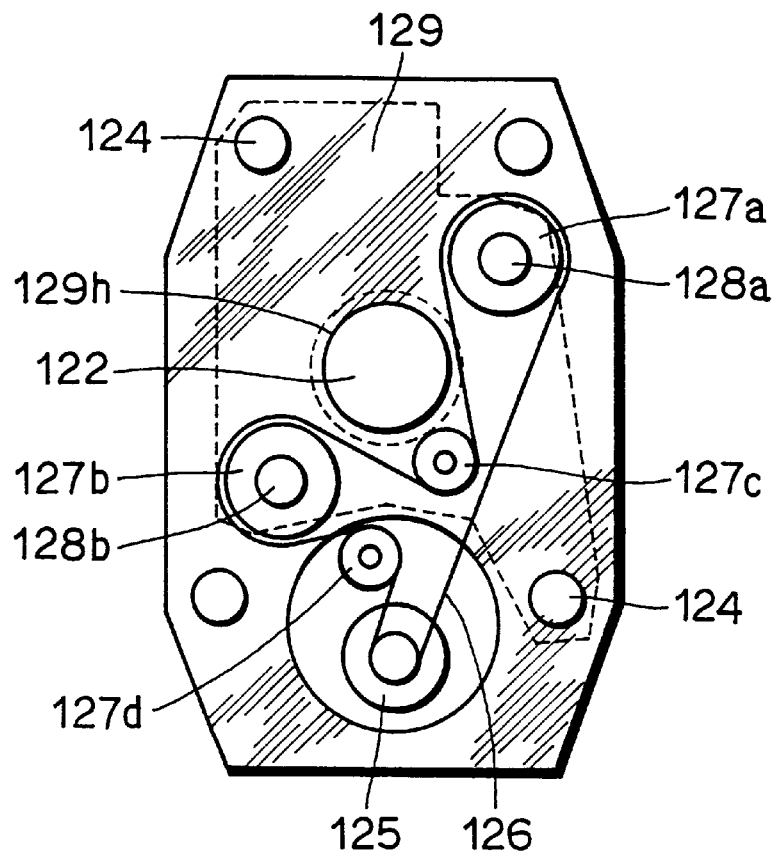
FIG. 17 shows an arrangement of internal units viewing from the rear side of the conventional medical injector head.
Figure 18:
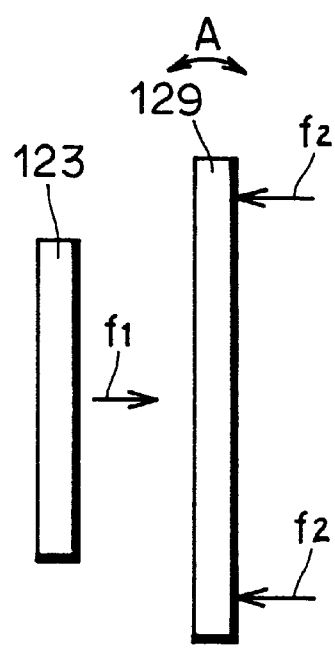
FIG. 18 is an illustration related to a problem of the conventional medical injector head.

According to the structure of the injector head for medical use in the first embodiment, the mechanism is simplified compared with the conventional structure of the injector head shown in FIG. 17 as illustrated in FIG. 4, since mechanical stopper 12 and position plate 20 are arranged on the same axis. As a result, the injector head can be scaled down. Note that FIG. 4 illustrates an arrangement of internal units viewing from the rear side of injector head for medical use 1A.

Figure 5:
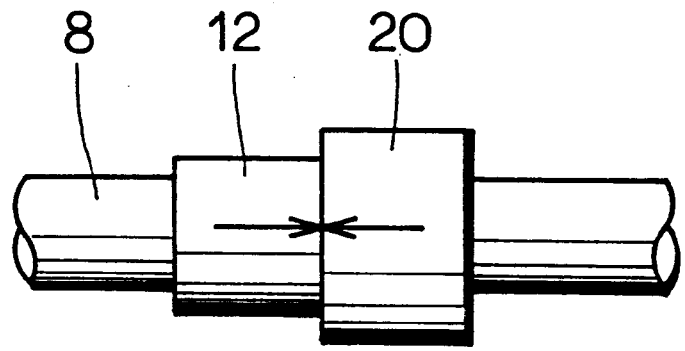

As shown in FIG. 5, mechanical stopper 12 and position plate 20 are placed on the same axis to allow their forces acting on each other to be generated on the axis of plunger. Accordingly, mechanical stopper 12 and position plate 20 can be moved in the stable state.

Figure 6:
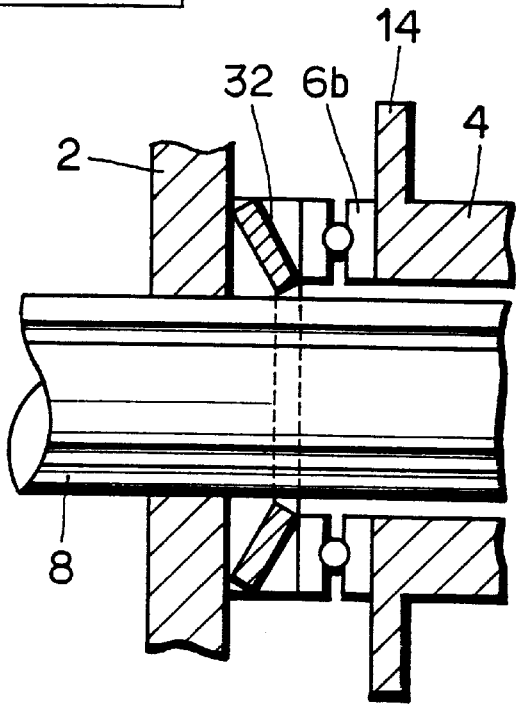
FIGS. 6–8 are respectively the first to the third illustrations related to a mechanism for detecting the contact of a position plate and a mechanical stopper.
Figure 7:
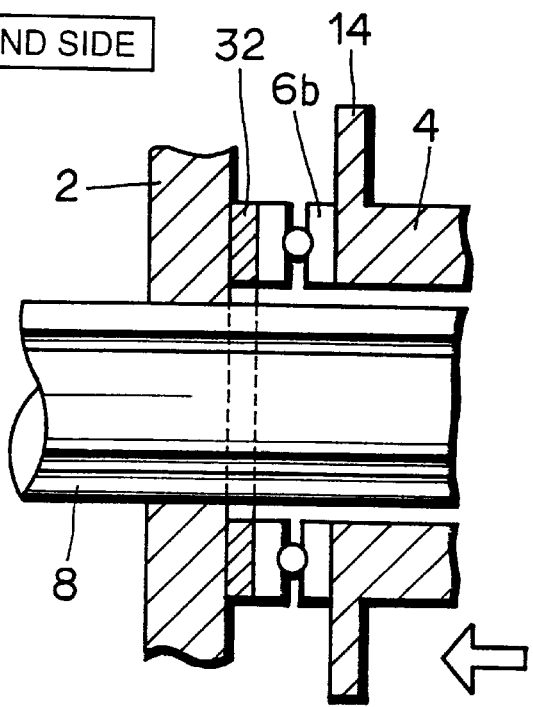
Figure 8:
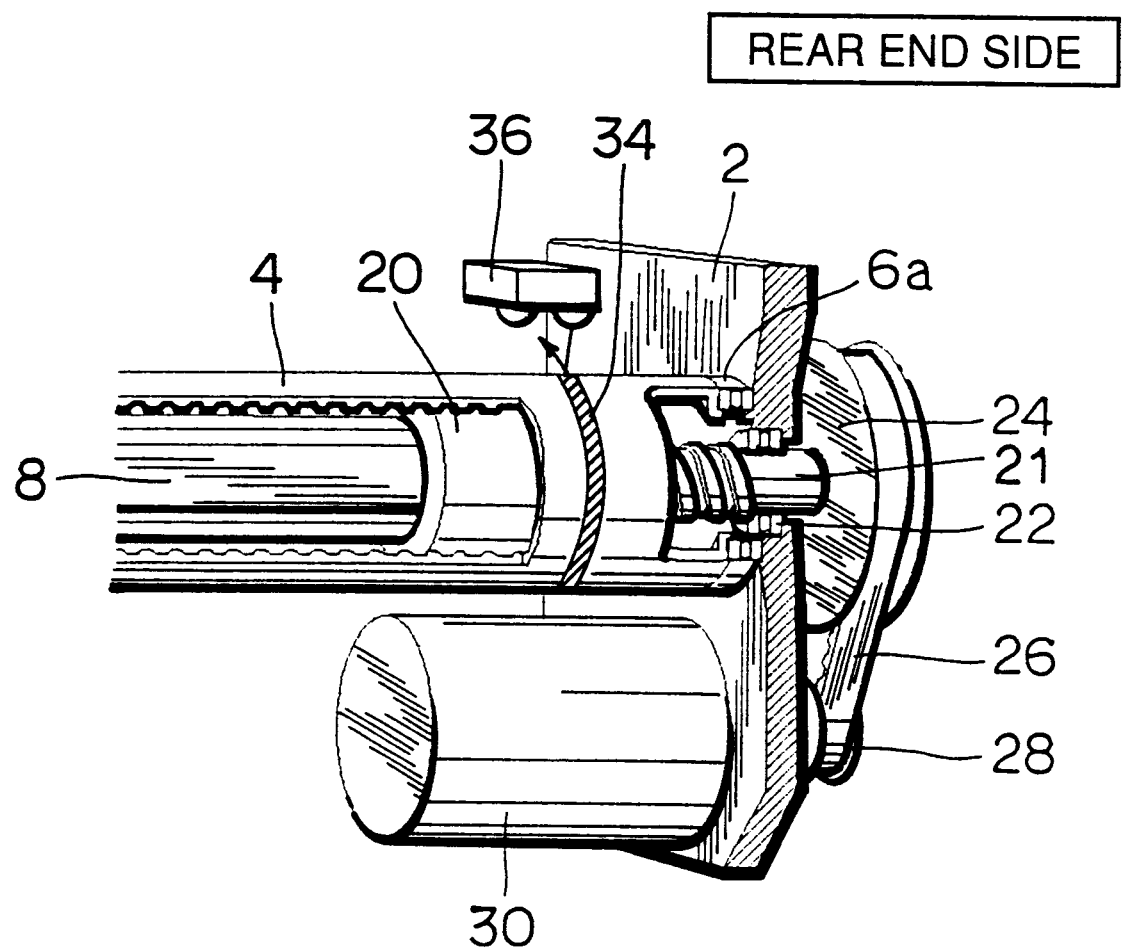

Referring to FIGS. 6–8, a mechanism for defecting that mechanical stopper 12 and position plate 20 meet in medical injector head 1A according to this embodiment will be described.

With reference to FIG. 6, a belleville spring 32 is provided between main body frame 2 and thrust bearing 6b as an elastic member at the front end side of main body portion 4. Belleville spring 32 allows a force which moves position plate 20 to the front end side to be transmitted to main body portion 4 via the nut portion of mechanical stopper 12 when position plate 20 is brought into contact with mechanical stopper 12. As a result, main body portion 4 moves against an urging force of belleville spring 32 as illustrated in FIG. 7.

Referring to FIG. 8, a unit for detecting the movement of main body portion 4 is described. The unit for detecting the movement of main body portion 4 can be constituted by providing, for example, a band-shaped mark 34 on the outer surface of main body portion 4 and a photosensor 36 which reads mark 34. Mark 34 moves with main body portion 4, so that the movement of main body portion 4 can be read using the change of the signals measured by the photosensor.

Although belleville spring 32 is provided at the front end side of main body portion 4 as one example, the elastic member may be any if it can urge main body portion 4 to the rear end side and can change its shape against the movement of main body portion 4. The unit for detecting the movement of main body portion 4 is not necessarily a device utilizing the photosensor. The movement of main body portion 4 may be detected by providing a projection to main body portion 4 and detecting the movement of the projection by a micro switch.

Figure 9:
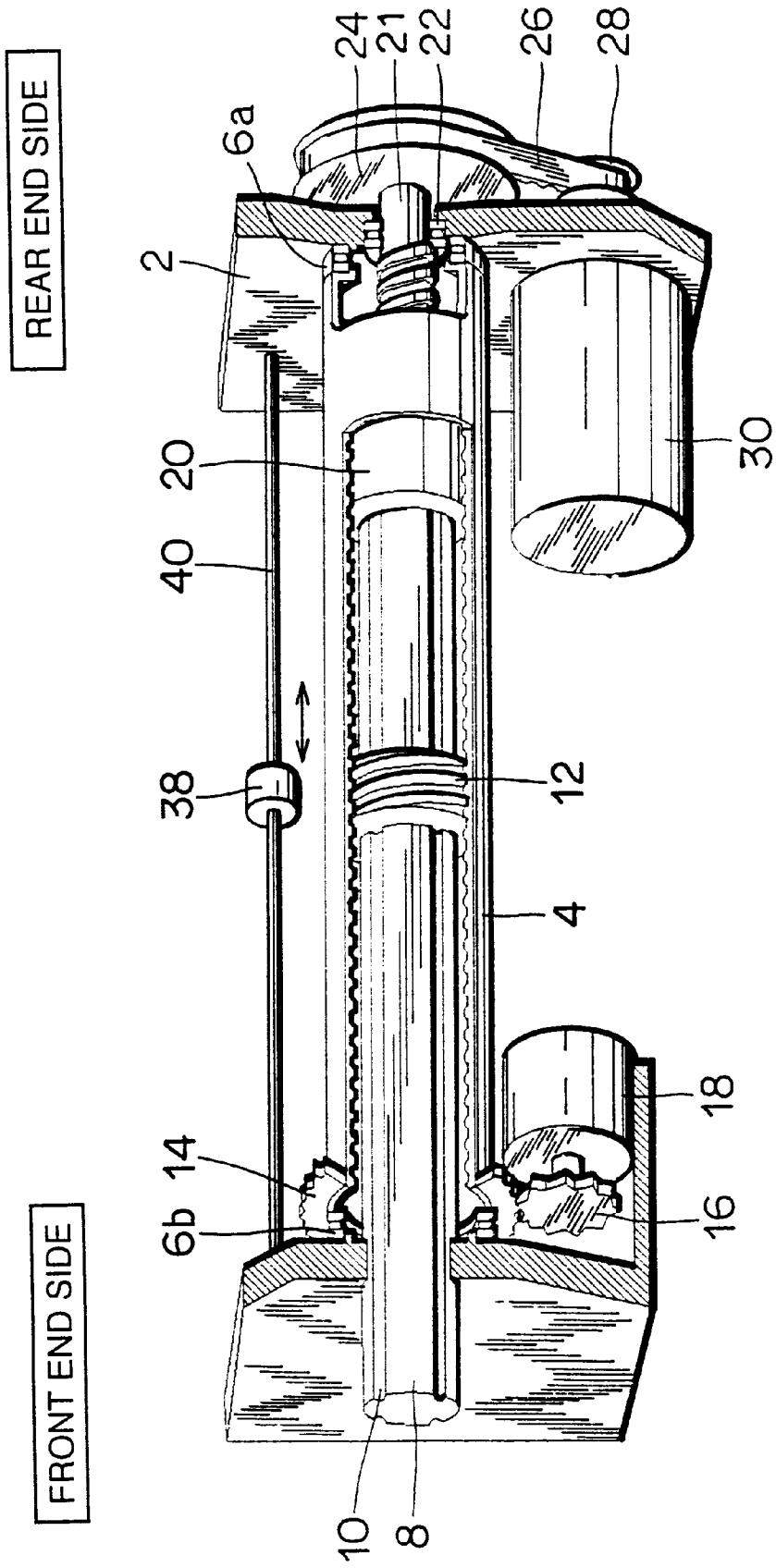
FIGS. 9 and 10 are provided for illustrating the first and second units for detecting the position of the mechanical stopper.
Figure 10:
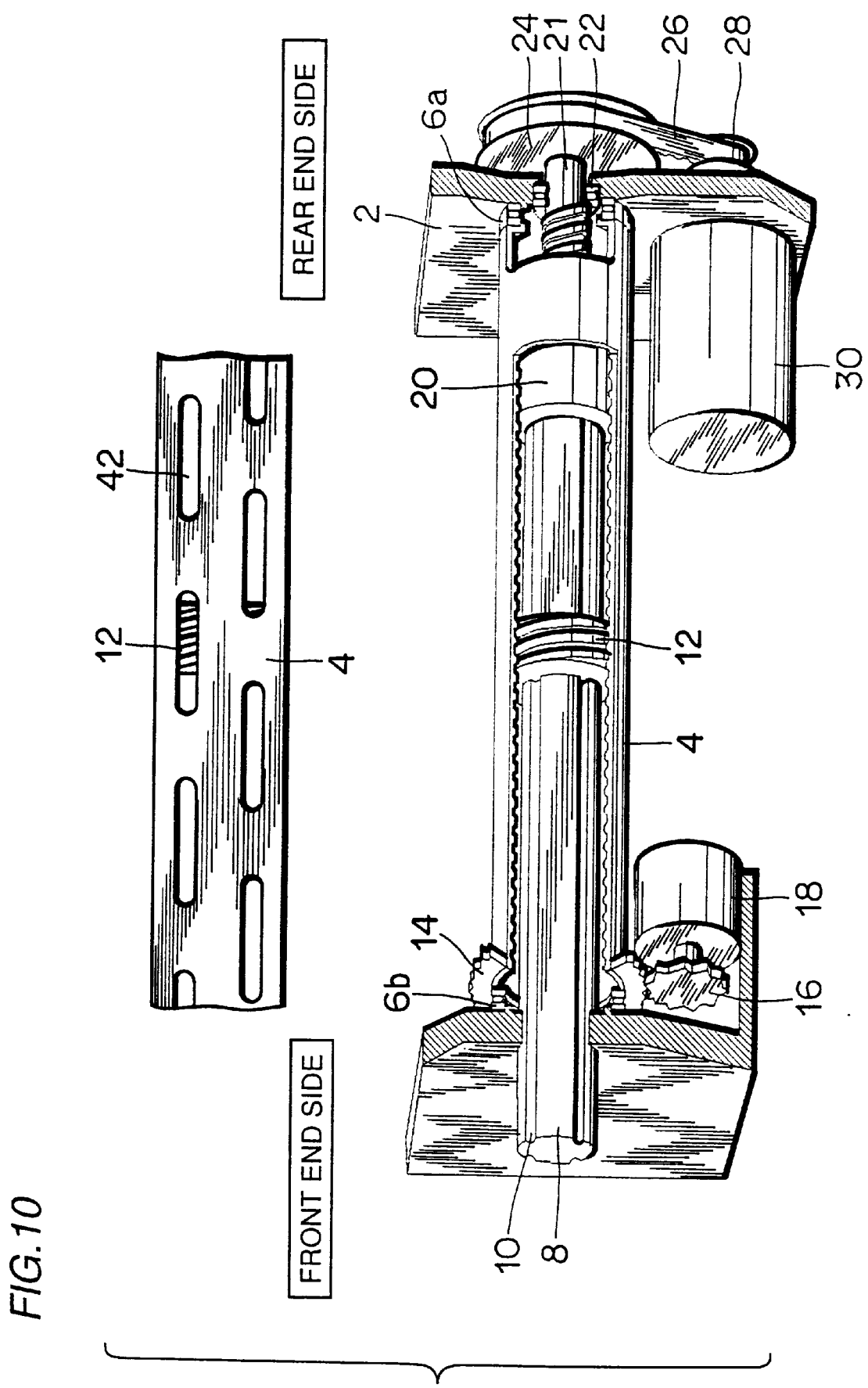

With reference to FIGS. 9 and 10, a mechanism for detecting the position of mechanical stopper 12 in main body portion 4 will be described.

Referring to FIG. 9, mechanical stopper 12 is formed of magnetic material and main body portion 4 is formed of non-magnetic material. A pointer 38 attracted according to the magnetic force of mechanical stopper 12 is provided on the outer surface of main body portion 4 such that it can move along a guide bar 40 placed at main body frame 2. Pointer 38 thus slides along guide bar 40 following the movement of mechanical stopper 12. Accordingly, the position of mechanical stopper 12 can be visually detected indirectly.

A mechanism for detecting the position of the mechanical stopper is further shown in FIG. 10. A slit 42 may be provided at the sidewall of main body portion 4. Slit 42 allows the position of mechanical stopper 12 to be visually detected directly.

Further, the position of mechanical stopper 12 may be detected indirectly by detecting the direction and angle of the rotation of main body portion 4 utilizing a potentiometer according to the relation between the male thread of main body portion 4 and the female thread of mechanical stopper 12.

Figure 11:
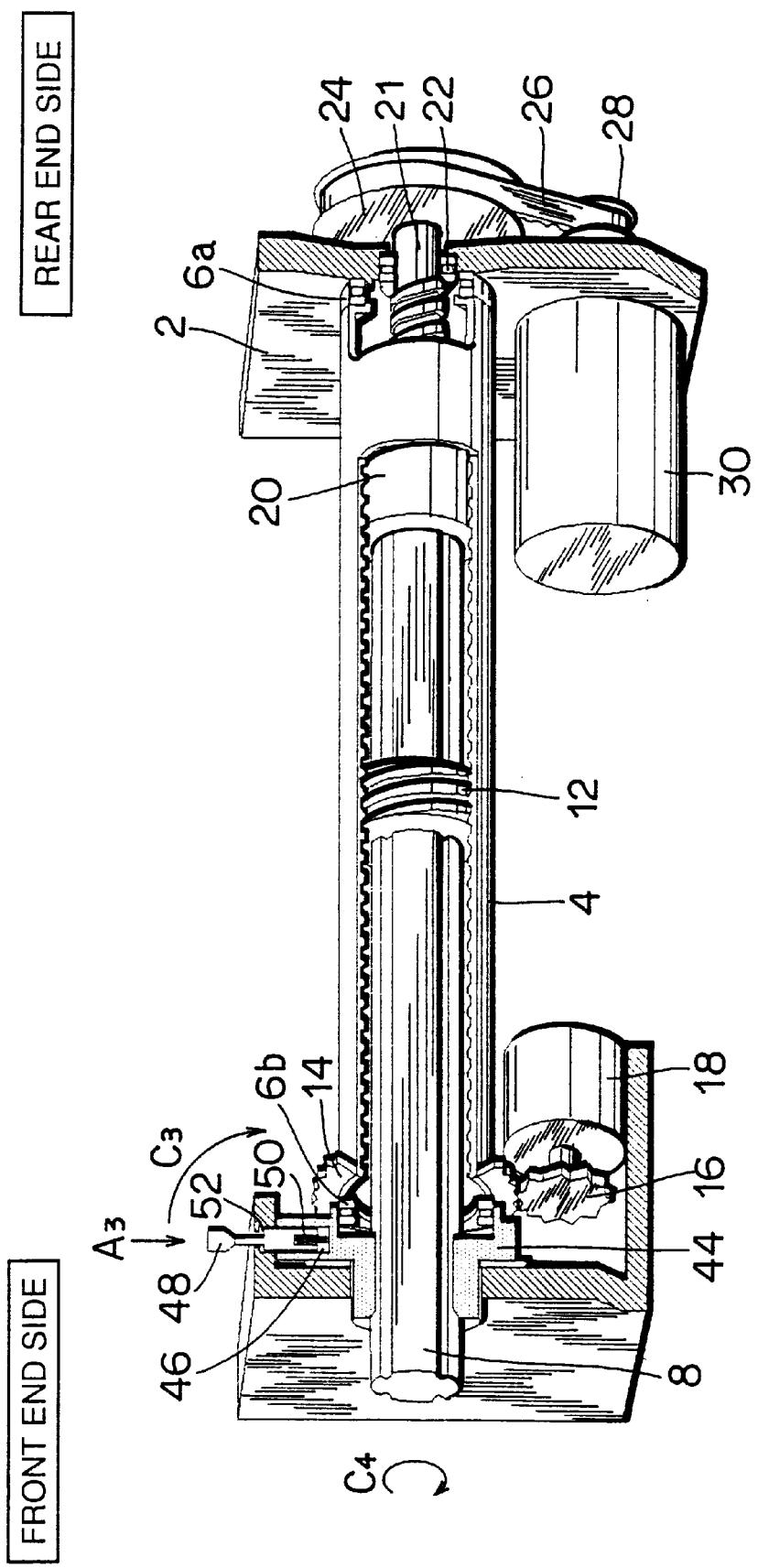
FIG. 11 is an illustration related to a mechanism for rotating a plunger by a prescribed angle.

Referring to FIG. 11, a mechanism is described for allowing plunger 8 to rotate by a prescribed angle in order to attach and detach plunger 8 to and from a piston provided in a syringe in medical injector head 1 having the structure described above.

In FIG. 11, a bush 44 which can rotate independently of main body frame 2 is provided at a support portion of main body frame 2 for plunger 8 in the medical injector head. Plunger 8 is passed through bush 44.

Although plunger 8 cannot rotate independently of bush 44, can rotate with bush 44 independently of frame 2.

Bush 44 is provided with locking mechanism for main body frame. In this locking mechanism, a pin 48 is inserted into a concave portion 46 in bush 44. Pin 48 is always urged by a spring 50 in a direction away from plunger 8. The urging force of spring 50 allows pin 48 to be inserted into concave portion 52 provided in main body frame 2.

Accordingly, in the normal state, pin 48 extends over concave portion 46 in bush 44 and concave portion 52 in main body frame 2. Main body frame 2 and bush 44 are thus coupled by pin 48 so that bush 44 cannot rotate independently of main body frame 2. When pin 48 is pushed down in the direction shown by an arrow $A_3$ against the urging force of spring 50, pin 48 is taken off from concave portion 52 of main body frame 2. Plunger 8 can thus be rotated by a prescribed angle to main body frame 2 by pushing pin 48 in the direction of arrow $A_3$ and rotating it in the direction shown by an arrow $C_3$. The mechanism thus provides an easy attachment and detachment of plunger 8 to and from a piston of a syringe.

(Second Embodiment)

Figure 12:
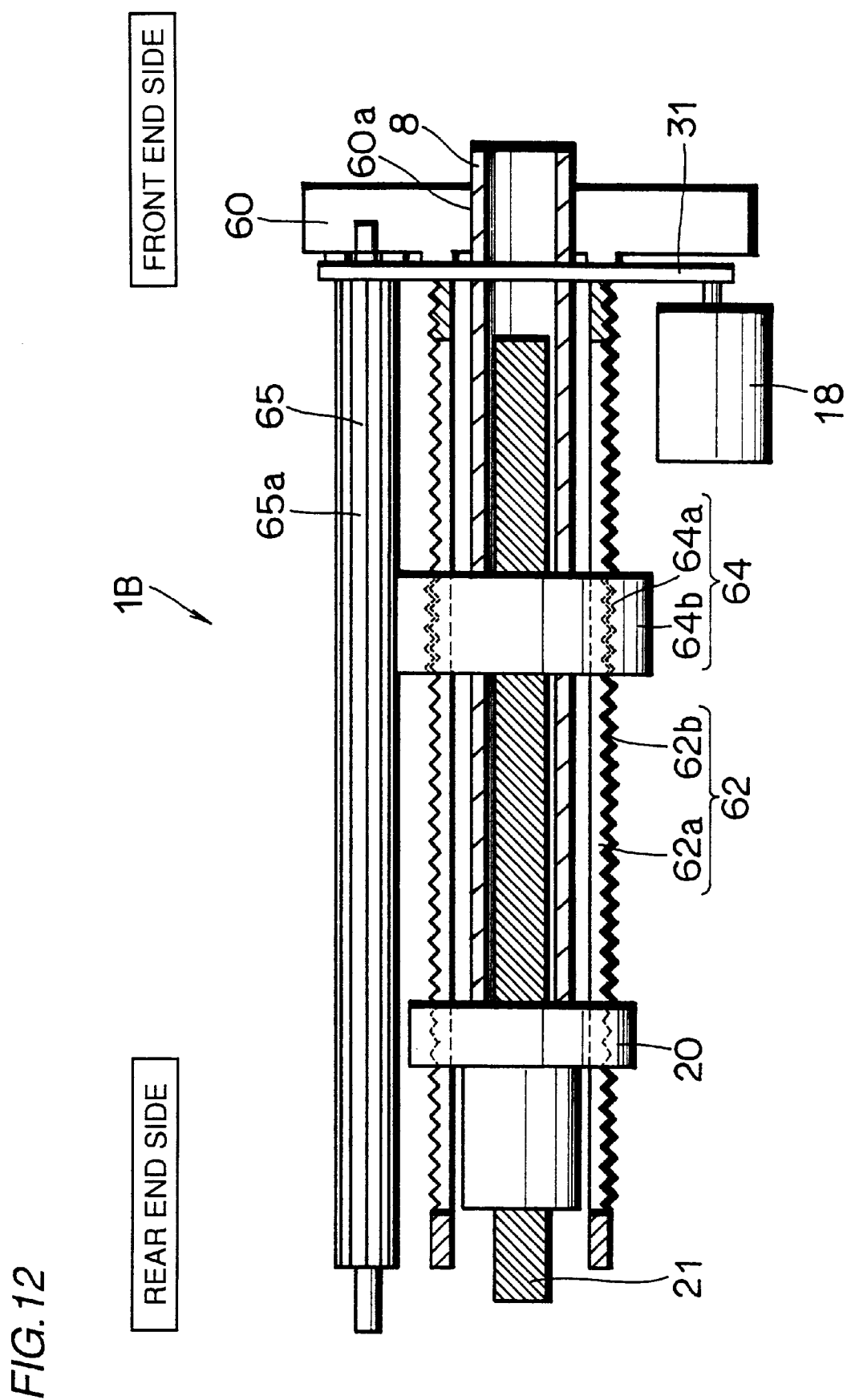
FIG. 12 is a partial cross sectional view of an injector head for medical use according to the second embodiment of the invention.

With reference to FIG. 12, a structure of an injector head for medical use according to the second embodiment will be described. Only plunger 8 and a main body frame 60 are shown by their cross sections for convenience of description.

An injector head for medical use 1B is provided with main body frame 60. Plunger 8 having its front end portion coupled to a piston of a syringe is passed through a slide hole 60a provided to main body frame 60 such that it can move in the direction of its axis. Plunger 8 is provided with a plurality of concave grooves (not shown) along its own axis as in the first embodiment. Slide hole 60a has convex portions (not shown) which are fit into the concave grooves for restraining plunger 8 from rotating on its axis.

At the rear end side of plunger 8, a cylindrical position plate 20 is arranged. Position plate 20 serves as both a position plate and a nut of a ball screw. The position plate and the nut of the ball screw may be provided as separate structures.

The front end portion of screw axis 21 of the ball screw is placed in an internal space of plunger 8 such that it does not interfere with plunger 8. A drive unit similar to the first embodiment (not shown) for rotating the screw axis is provided at the rear end portion of screw axis 21 of the ball screw.

A cylindrical main body portion 62 is fixed to main body frame 60 to cover some portions of plunger 8, screw axis 21, and position plate 20. Slit holes 62a for exposing a part of position plate 20 are provided to main body portion 62 at two locations along its axis. A male thread 62b is formed on the outer surface of main body portion 62.

A mechanical stopper 64 is placed ahead of position plate 20 at plunger 8. A female thread 64a formed on the internal surface of mechanical stopper 64 and male thread 62b of main body portion 62 are screwed together. A first gear 64b is formed on the outer surface of mechanical stopper 64.

A gear bar 65 having a second gear 65a formed on its outer surface engaging with the first gear 64b formed on the outer surface of mechanical stopper 64 is provided to main body frame 60 in parallel with main body portion 62. Driving force of mechanical stop motor 18 provided to main body frame 60 is transmitted to gear bar 65 via a belt 31.

Figure 13:
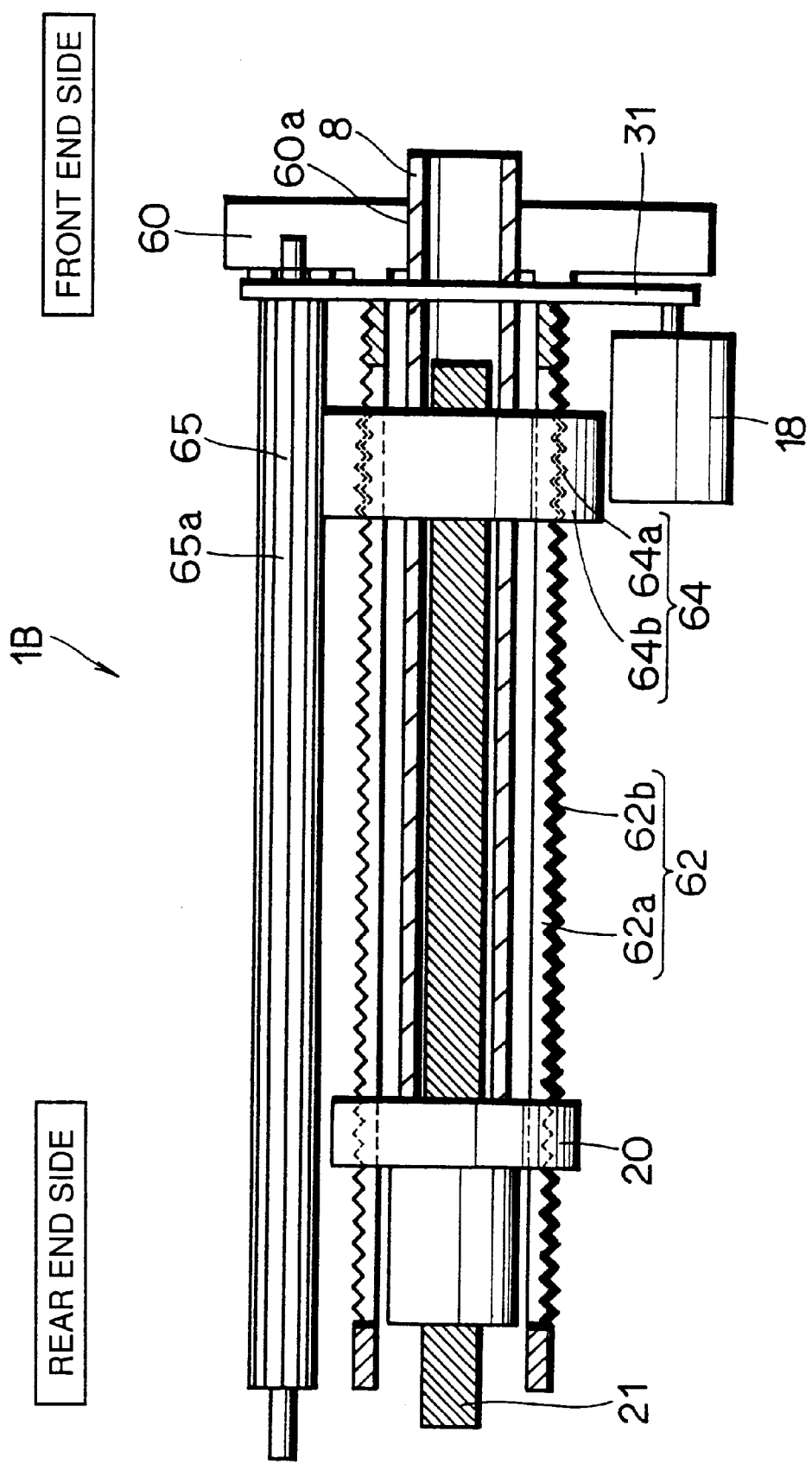
FIGS. 13 and 14 are respectively the first and second illustrations related to an operation of the injector head for medical use according to the second embodiment.
Figure 14:
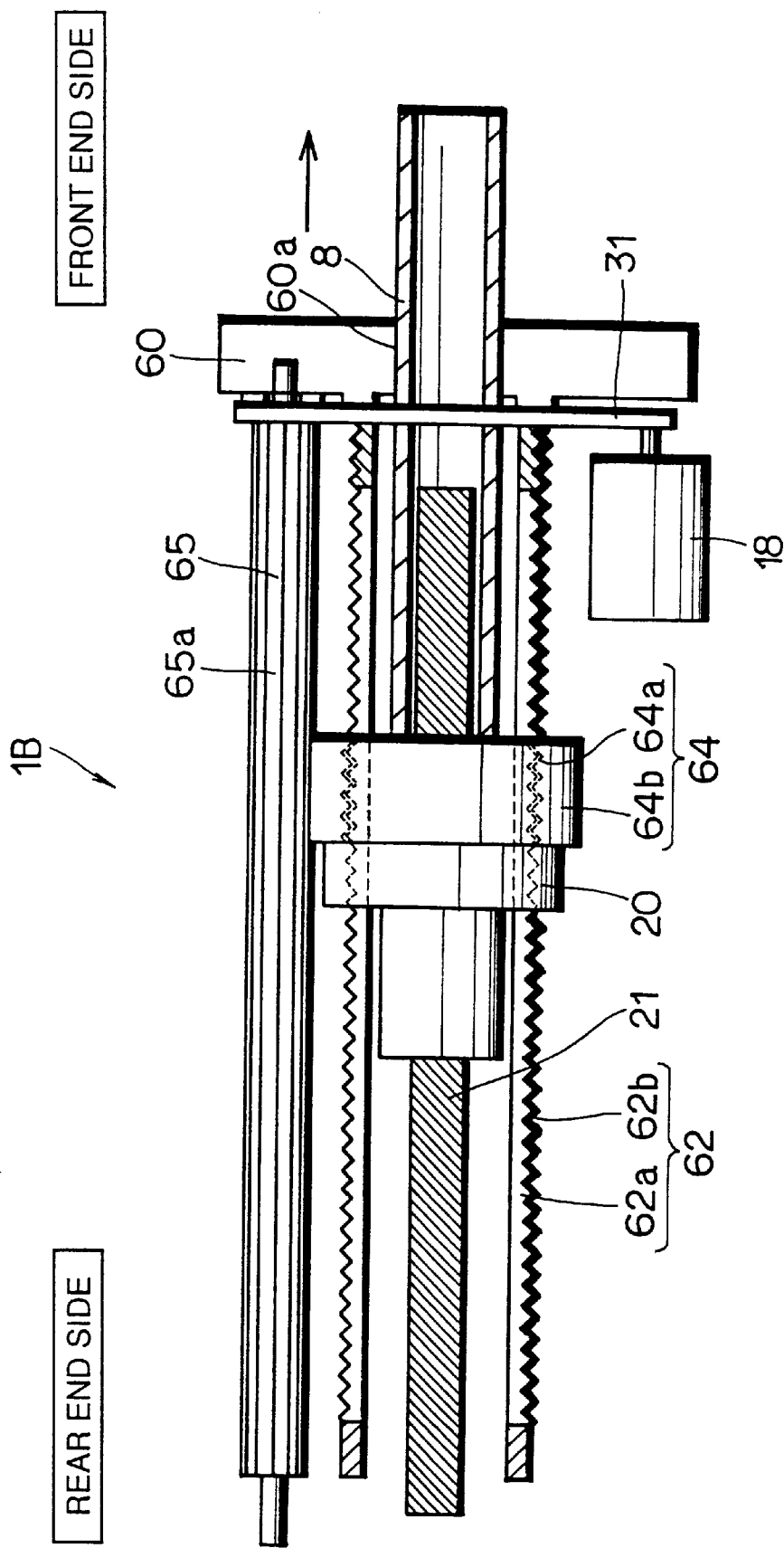
Figure 15:
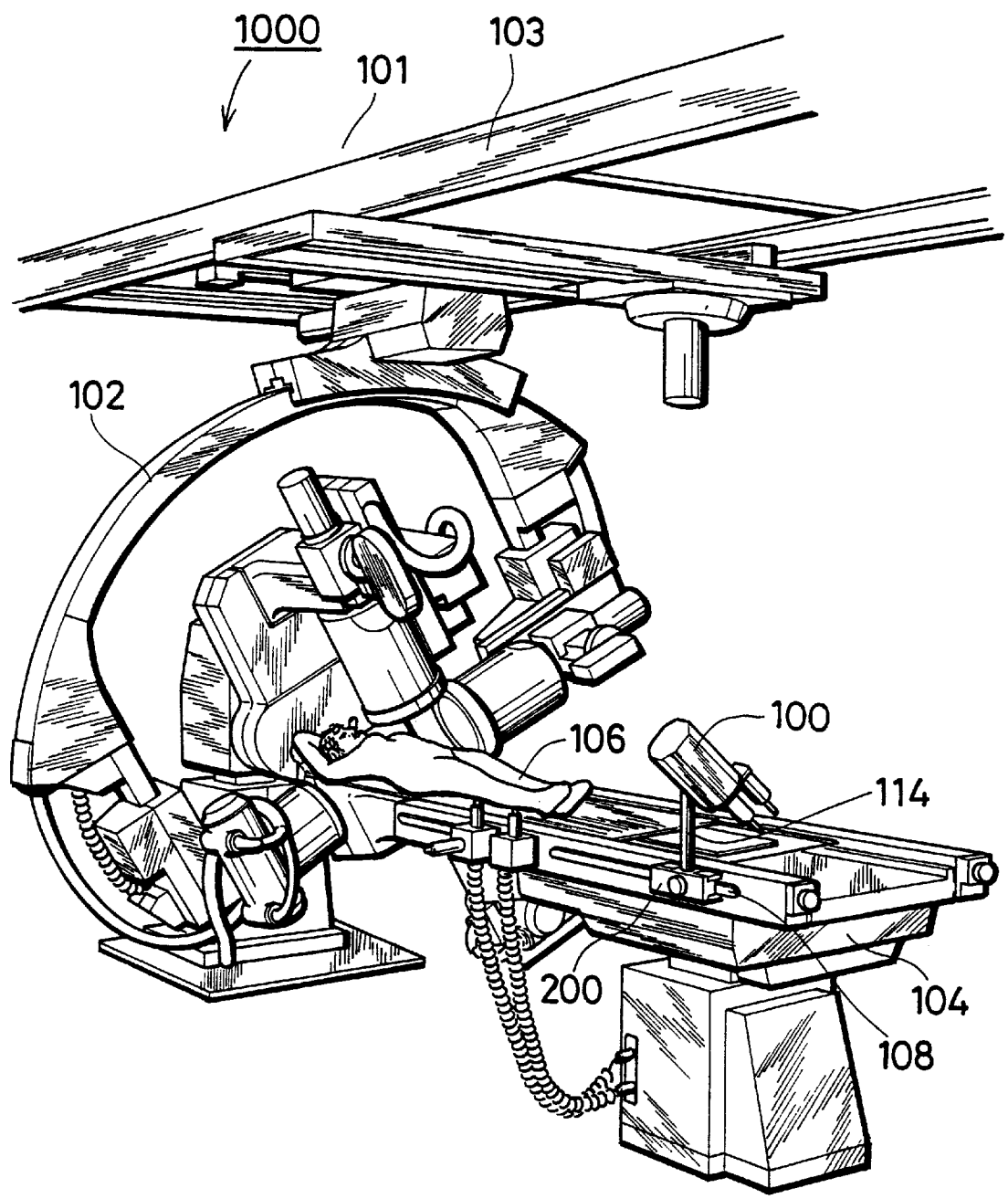
FIG. 15 is an illustration showing an entire structure of a circulatory organ X-ray diagnostic apparatus.
Figure 16:
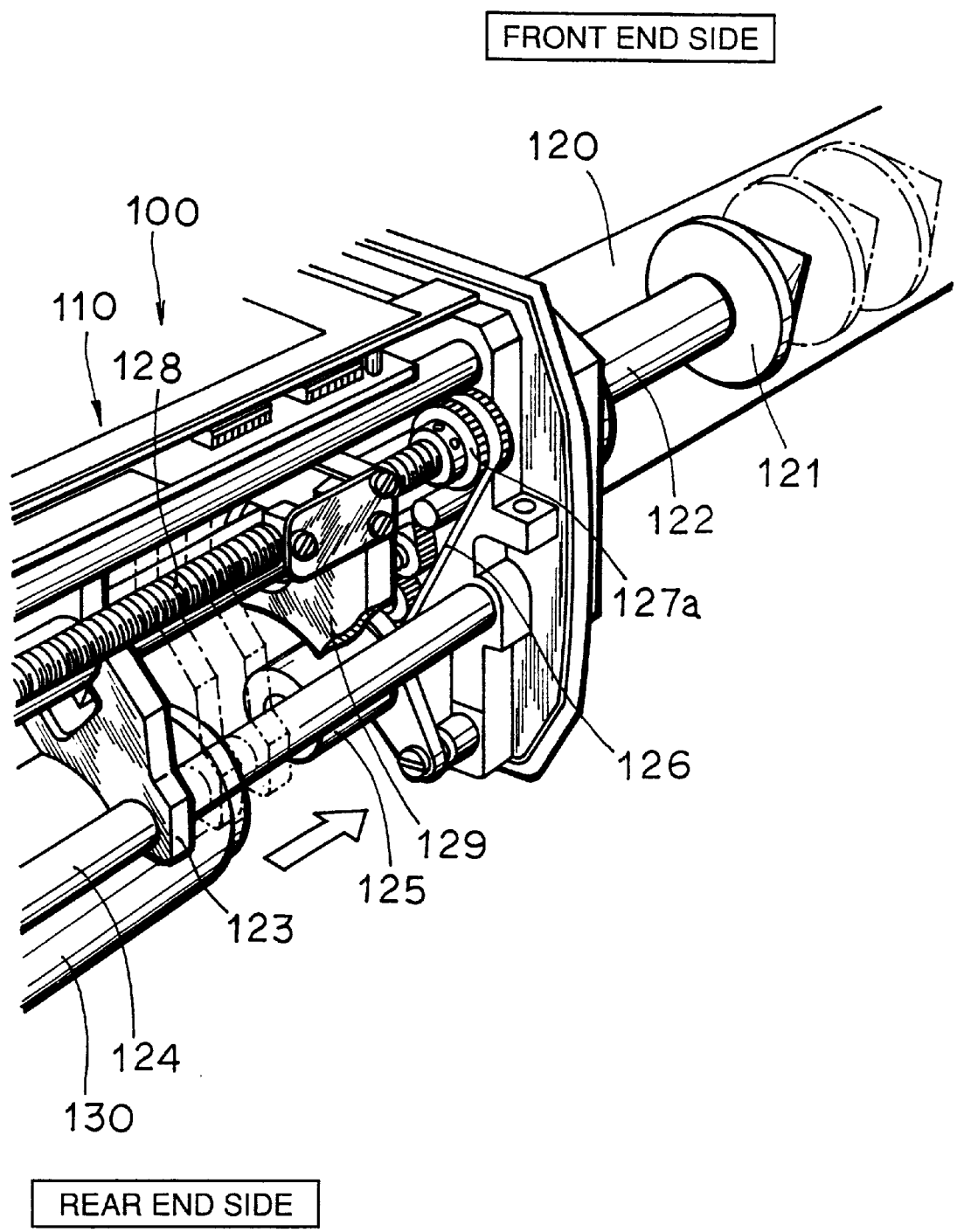
FIG. 16 is a perspective view illustrating an internal structure of a conventional injector head for medical use.

Referring to FIGS. 13 and 14, an operation of medical injector head 1B having the structure described above will be described.

Referring to FIG. 13 first, a method of driving mechanical stopper 64 is described. Mechanical stop motor 18 is rotated to rotate gear bar 65 in order to drive mechanical stopper 64. The rotation of gear bar 65 causes the rotation of mechanical stopper 64 to enable mechanical stopper 64 to move along the axis of plunger 8, as a result of the relation between the female thread formed on the inner surface of mechanical stopper 64 and the male thread 62b formed on the outer surface of main body portion 62. Accordingly, the position of mechanical stopper 64 is controlled by controlling mechanical stop motor 18.

Next with reference to FIG. 14, the position control of position plate 20 is described. Similar to the first embodiment, the position plate and plunger 8 can be moved by rotating screw axis 21 by a prescribed degree using a drive unit (not shown). The position of position plate 20 is thus moved.

In the structure of the medical injector head according to the second embodiment, the mechanism is simplified and the injector head can be scaled down by utilizing the structure in which mechanical stopper 64 and position plate 20 are placed on the same axis as in the medical injector head according to the first embodiment.

The placement of mechanical stopper 64 and position plate 20 on the same axis produces forces that is acting on each other on the axis of plunger 8. As a result, mechanical stopper 64 and position plate 20 can be moved in the stable state.

According to this embodiment, an operational effect similar to that of the first embodiment can be obtained by employing a mechanism for detecting that the mechanical stopper and the position plate are come into contact with each other described referring to FIGS. 6–8, a mechanism for detecting the position of the mechanical stopper described referring to FIGS. 9 and 10, and a mechanism for rotating the plunger by a prescribed angle described referring to FIG. 11.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. An injector head for medical use having a syringe attached thereto, the syringe including a cylindrical body portion having an inject portion and an opening portion respectively at a front end side and a rear end side and including a piston defining an internal space for sucking in contrast medium to be injected to a patient and provided movably between the front end side and the rear end side of said body portion, comprising:

a plunger having its front end portion coupled to said piston, capable of reciprocating in a direction of movement of said piston, and restrained from rotating on its axis;

first drive means provided at a rear end side of said plunger for reciprocating said plunger;

a mechanical stopper through which said plunger passes, provided such that it is capable of moving along the axis of said plunger and is restrained from rotating on the axis of said plunger;

move and fix means for moving said mechanical stopper along the axis of said plunger and fixing it at an arbitrary position by engaging with said mechanical stopper while rotating on the axis of said plunger;

second drive means for rotating said move and fix means;

a position plate provided at the rear end side of said plunger to the rear of said mechanical stopper for preventing said plunger from moving by contacting with said mechanical stopper when said plunger moves to the front end side; and a frame for supporting said plunger, said first drive means, said mechanical stopper, said move and fix means, and said position plate.

2. The injector head for medical use according to claim 1, wherein said first drive means includes:

a ball screw having a screw axis placed within said plunger and a nut provided at the rear end side of said plunger screwed together with the screw axis; and a drive mechanism for applying a turning force to said screw axis, and said nut serves as said position plate.

3. The injector head for medical use according to claim 2, wherein said plunger includes at least one of a first concave and convex position formed on its surface along its axis and is supported by said frame at its front end portion such that it can slide member and is restrained from rotating, said mechanical stopper includes at least one of a second concave and convex portion engaging with said at least one of first concave and convex portion as well as a first thread groove respectively formed on its inner surface and on its outer surface, and said move and fix means has a cylindrical shape accommodating said plunger, said ball screw, and said position plate, and includes a second thread groove on its inner surface screwed together with said first thread groove of said mechanical stopper.

4. The injector head for medical use according to claim 3, wherein said move and fix means further includes detect means for detecting that said position plate meets said mechanical stopper.

5. An injector head for medical use according to claim 3, wherein said frame includes plunger rotation means for selectively rotating said plunger by a prescribed angle.

6. The injector head for medical use according to claim 2, wherein said plunger is supported by said frame at its front end portion such that it can slide and is restrained from rotating, said mechanical stopper includes a first thread groove and a second thread groove respectively on its inner surface and its outer surface, and said move and fix means has a cylindrical shape accommodating some parts of said plunger and said nut of said ball screw and includes:

a main body portion having a second thread groove screwed together with said first thread groove and a slit groove for exposing a part of said nut of said ball screw on its outer surface; and a gear having a third thread groove screwed together with said second thread groove of said mechanical stopper formed on its surface, the gear placed in parallel with said main body portion along a direction of the axis of said plunger.

7. The injector head for medical use according to claim 6, wherein said move and fix means further includes detection means for detecting that said position plate meets said mechanical stopper.

8. The injector head for medical use according to claim 6, wherein said frame includes plunger rotation means for selectively rotating said plunger by a prescribed angle.

* * * * *